(12) United States Patent
Mijers et al.

(10) Patent No.: US 11,491,085 B2
(45) Date of Patent: Nov. 8, 2022

(54) TRANSFER DEVICE FOR FLUID TRANSMISSION

(71) Applicant: Jan Willem Marinus Mijers, Haarlem (NL)

(72) Inventors: Jan Willem Marinus Mijers, Heemstede (NL); Matthew Robert Bryan, Tring Hertfordshire (GB)

(73) Assignee: Jan Willem Marinus Mijers, Haarlem (NL)

( * ) Notice: Subject to any disclaimer, the term of this patent is extended or adjusted under 35 U.S.C. 154(b) by 351 days.

(21) Appl. No.: 16/623,855

(22) PCT Filed: Jun. 21, 2018

(86) PCT No.: PCT/GB2018/051740
§ 371 (c)(1),
(2) Date: Dec. 18, 2019

(87) PCT Pub. No.: WO2018/234818
PCT Pub. Date: Dec. 27, 2018

(65) Prior Publication Data
US 2020/0146939 A1 May 14, 2020

(30) Foreign Application Priority Data
Jun. 21, 2017 (DE) .......................... 102017005791.5

(51) Int. Cl.
*A61J 1/20* (2006.01)
*A61M 5/178* (2006.01)

(52) U.S. Cl.
CPC ........... *A61J 1/2096* (2013.01); *A61J 1/2013* (2015.05); *A61J 1/2037* (2015.05); *A61J 1/2051* (2015.05);
(Continued)

(58) Field of Classification Search
CPC ...... A61J 1/2096; A61J 1/2013; A61J 1/2037; A61J 1/2051; A61J 1/2055; A61J 1/2075;
(Continued)

(56) References Cited

U.S. PATENT DOCUMENTS

| 6,159,192 | A | 12/2000 | Fowles |
| 2007/0079894 | A1* | 4/2007 | Kraus ................... A61J 1/2058 141/319 |

(Continued)

FOREIGN PATENT DOCUMENTS

| DE | 102015201285 B3 | 6/2016 |
| WO | 2014150674 A2 | 9/2014 |

*Primary Examiner* — Philip R Wiest
*Assistant Examiner* — Alessandro R Del Priore
(74) *Attorney, Agent, or Firm* — Michael Soderman

(57) ABSTRACT

A transfer device 2 for fluid transmission from a storage bottle 1 to a receiving unit, comprising at least one housing with a housing insert or inset which comprises at least one transfer needle 8, 9 and a needle protector. To ensure sufficient safety for the personnel, a new transfer device 2 is suggested which is suited for screwing on a disposable syringe 3 and may be directly connected to a storage bottle 1. Here, the transfer device 2 consists of only few elements which on the one hand ensure a reliable function and on the other hand prevent any contact with toxic medicine. To this end, the housing has a tubular design and has at one end an open cylinder section with at least one locking unit for a storage bottle 1, and at the other end an opening for a housing insert.

16 Claims, 10 Drawing Sheets

(52) U.S. Cl.
CPC ........... *A61J 1/2055* (2015.05); *A61J 1/2075* (2015.05); *A61J 1/2082* (2015.05); *A61M 5/1782* (2013.01)

(58) Field of Classification Search
CPC ...... A61J 1/2082; A61J 1/2017; A61J 1/2072; A61J 1/2089; A61M 5/1782
See application file for complete search history.

(56) References Cited

U.S. PATENT DOCUMENTS

| | | | |
|---|---|---|---|
| 2013/0076019 A1 | 3/2013 | Takemoto | |
| 2014/0276649 A1* | 9/2014 | Ivosevic | A61J 1/2048 604/533 |
| 2014/0361045 A1 | 12/2014 | Harman | |
| 2017/0367931 A1* | 12/2017 | Eichelkraut | A61J 1/2075 |
| 2019/0000717 A1* | 1/2019 | Fangrow | A61J 1/2082 |
| 2020/0113785 A1* | 4/2020 | Lopez | A61M 39/22 |

* cited by examiner

TRANSFER DEVICE FOR FLUID TRANSMISSION

CROSS REFERENCE TO RELATED APPLICATIONS

This application is the U.S. national stage of International Application No. PCT/GB2018/051740, filed on Jun. 21, 2018. The international application claims the priority of DE 102017005791.5 filed on Jun. 21, 2017; all applications are incorporated by reference herein in their entirety.

BACKGROUND

The invention relates to a transfer device for fluid transmission, e.g. such as fluids comprising toxic material or toxic medicine, from a storage bottle to a receiving unit. The invention relates particularly, but not exclusively, to a transfer device comprising at least one housing with a housing inset or insert comprising at least one transfer needle and a needle protector.

Generic transfer devices are required for toxic fluids such as medicine, particular care being taken that the transfer needles coming into contact with the medicine are sufficiently protected. For this reason, such medicine is filled into storage bottles which are provided with a closure comprising a puncturable rubber membrane, often referred to as a septum. The storage bottles are not opened by the personnel in the hospital, in particular nurses; instead, the medicine is withdrawn from (sucked out of) the storage bottle by means of a transfer needle and a disposable syringe. The transfer needle punctures the puncturable rubber membrane to access the fluid within the storage bottle. After the removal of the transfer needle from the storage bottle, the rubber seal closes around the puncture formed by the needle and completely closes the storage bottle so that there is no risk of the fluid/medicine dripping from the puncture.

The transfer devices here consist of the required transfer needle and a housing where the transfer needle is accommodated. The transfer device is thus used on the one hand for adapting a storage bottle, and moreover, a commercially available disposable syringe may be screwed on, for example via a Luer-Lock connection, so that the desired amount of medicine may be withdrawn, i.e. sucked out of the storage bottle. In this process, the inventors have realised that it is desirable to provide air pressure compensation so that no vacuum (i.e. pressure drop relative to ambient pressure) is formed in the storage bottle, and that it is desirable that air is allowed simultaneously into the storage bottle via an air duct while fluid is withdrawn from the storage bottle.

A disadvantage in prior art is that in the handling of the transfer device, it may not be possible to prevent droplets of fluid escaping from the storage bottle, for example via the provided air duct, and thus there is a risk of skin contact. This risk is especially present when, during handling, any air bubbles are to be removed from the chamber volume of the disposable syringe. A common procedure for bubble removal is that a portion of the medicine, with the air bubbles entrained, is pushed back into the storage bottle. However, as a result of this procedure, an overpressure may build up in the storage bottle which leads to not only air, but also the medicine being able to escape via the air duct.

SUMMARY

It is an object of the present invention to provide a transfer device which overcomes the disadvantages known from prior art and consists of a small number of individual parts. According to the invention, the housing is formed as a tube with an open cylinder part with at least one locking unit on the one end and an opening for the housing inlet on the other end. According to the present invention there is provided an apparatus and method as set forth in the appended claims. Other features of the invention will be apparent from the dependent claims, and the description which follows.

DETAILED DESCRIPTION

In a first aspect, the invention provides a transfer device for fluid transmission, in particular of toxic medicine, from a storage bottle to a receiving unit, comprising at least one housing with a housing insert or inset comprising at least one transfer needle and one needle protector. The housing has a tubular design and comprises, at one end, an open cylinder section with at least one locking unit for a storage bottle, and at the other end an opening for the housing insert or inset.

The housing insert or inset may comprise an intermediate part which comprises, in the axial direction towards the radial bottom surface, integrally moulded first and second nozzles or pins (i.e. pin-shaped nozzle) whereby a respective one such pin or nozzle is disposed on a respective one of each/both sides of the intermediate part. The intermediate part may define an indentation, recess, cavity or receptacle (e.g. a pot-like, bowl-like or cup-like).

Desirably, a through bore extends through the nozzles/pins.

A first pin may be disposed to be protruding from the bottom surface of the intermediate part to the outside. The first pin may be provided for shifting on a needle protector. A second pin may be disposed to be protruding from the bottom surface of the intermediate part in a direction into/within the recess of the indentation (e.g. recess, cavity or receptacle, a pot-like, bowl-like or cup-like form) for centring.

The indentation (e.g. recess, cavity or receptacle, a pot-like, bowl-like or cup-like form) may be closable with a lid part to which a third pin/nozzle is integrally formed or moulded. The third pin/nozzle may be provided with a Luer-Lock thread, e.g. upon its outer surface.

The intermediate part and the lid may be connectable or connected together (e.g. mechanically, via locking elements) or may be connected together welding (e.g. by laser welding) to each other.

A valve disk, and/or a valve seal, and/or a filter frame with openings, and/or a hydrophobic membrane filter and/or an activated-carbon filter, may be located in the indentation (e.g. recess, cavity or receptacle, a pot-like, bowl-like or cup-like form).

The needle protector may comprise an elastic material (e.g. an elastomer, such as a rubber material). The needle protector may comprise at one end a bore which is provided for receiving a second pin/nozzle of the bottom surface. The needle protector may comprise a contractably expandable structure with pleated or concertinaed sides expansible to allow it to expand and contract axially. In this sense, the structure of the needle protector may be a bellows-like shape or an accordion-like shape. The axis of the needle protector may be parallel or coaxial with the axis of the needle(s) it protects. The needle protector may comprise a seal part at or adjacent an end of the needle protector which is annular and/or shaped as a disc extending (e.g. radially) towards the inner wall of the housing to form a sliding seal therewith. Preferably the sliding seal extends all the way around the needle protector to form a continuous and closed seal. The seal part may form a sliding interface with the inner wall of the housing for guiding axial movement of the needle protector during compression and expansion thereof. The seal part may be integrally formed with the contractably expandable structure. The seal part may be formed from a material having a Shore Hardness which is less than the Shore Hardness of the contractably expandable structure. For example, the Shore Hardness of the seal part may be no greater than 60%, or optionally no greater than 50%, or optionally no greater than 40%, of the value of the Shore Hardness of the contractably expandable structure. The seal part may be formed from an elastic material having a Shore Hardness (S) of between 30 and 40, e.g. S=35. The contractably expandable structure may be formed from an elastic material having a Shore Hardness (S) of between 60 and 80, e.g. S=70. The Shore Hardness (S) may be measured according to the following standard: ASTM D2240 (e.g. scale/type A Hardness). The relatively less hard material of the seal part permits it to deform, comply, adapt of re-shape more easily and effectively to reciprocate/complement the shape of an end of a storage bottle (e.g. septum) when pressed against it in use. A fluid-tight seal is more effectively produced as a result. In addition, the softer material permits a more effective closure/sealing of a puncture formed within it by a needle after the needle is removed/withdrawn from the seal, and retracted back inside the needle protector. The relatively larger hardness of the contractably expandable structure provides a 'springiness' which assists in allowing the structure to expand to recover its original, quiescent shape and dimensions once the storage bottle is removed and no pressure is applied to the needle protector. The transfer needle may be protected by the contractably expandable structure (e.g. an accordion-like) as a needle protector formed of an elastic material. The needle protector may be, at one end thereof, placed on the housing inset/insert and, at the other end thereof, may comprise an annular elastic or elastomeric (e.g. rubber) seal, e.g. the guide seal described above, which is provided for abutment against a rubber/ elastic/elastomer seal or septum of the storage bottle.

The needle protector may comprise a disc (e.g. the seal part) and a cylindrical elevation on the side of the disc facing outwards. The cylindrical elevation may be integrally formed with the disc, and may be of the same material (i.e. Shore Hardness).

The elevation may comprise a centrical surface which may be adapted to be punctured by at least one said needle, and/or the centrical surface may be disposed to come to lie against a seal/septum of the storage bottle in use.

The needle protector may be arranged such that, when the transfer device is placed onto a storage bottle compressed in the axial direction (e.g. against the bottle septum), the needle(s) within the needle protector come out of the needle protector centrical surface (i.e. through that surface, as the needle protector is withdrawn/compressed about the needle (s)).

The needle protector may be configured to receive two transfer needles, one transfer needle may be provided for sucking liquid out of the storage bottle, and a second transfer needle may be provided for air supply. Additionally or alternatively, the second transfer needle may form an air duct which is connected to the outside air via a filter arrangement.

The air duct may be sealed by a valve seal which is arranged to open when air enters, and to remain in a closed position when an overpressure is present in the storage bottle.

The valve seal may be equipped with a one-sided edge swelling, and/or a filter frame and/or a filter disk may be equipped with an edge-sided bulge.

The cylinder section may comprise, by two diametrically opposed recesses each, a tube wall section formed between the recesses.

The tube wall section may be equipped at one end with a locking hook and may comprise at the other end a pressing surface protruding from the tube wall section, and/or the tube wall section may be arranged to be only connected with the housing via a web in an elastically/resiliently deformable/movable manner.

The tubular housing offers the possibility of using at one end a locking unit for the storage bottle, and at the other end a housing insert or inset insertable into the housing whereby the number of individual parts may be clearly reduced. Moreover, the cylindrical shape ensures a stable housing which may be directly placed onto the storage bottle. The at least one transfer needle is here located within the housing and can only axially protrude from the interior when the transfer device is placed onto the storage bottle. The transfer needles themselves are additionally protected by an elastic membrane which, due to its restoring force, completely encloses the transfer needle again when it is removed from the storage bottle.

In one development of the invention, the housing insert or inset consists of a pot-like intermediate part which comprises, in the axial direction towards a radial bottom surface, one integrally formed first and second pin each on both sides. It is to be understood that the term 'pot-like' is intended to be a reference to an indentation, recess, cavity or receptacle, which is describable as e.g. a pot-like, bowl-like or cup-like form, unless otherwise implied or stated. The housing insert or inset may here be inserted into the open end of the tubular housing and will simultaneously seal the latter on one side of the cylindrical housing whereby a permanent connection is formed by welding, in particular laser welding.

The housing insert or inset consists of a pot-like intermediate part with a bottom surface, and integrally and centrically formed nozzles/pins on both sides of the bottom surface in the axial direction. It is to be understood that references to 'pins' herein, are intended to refer to pin-like nozzles, unless otherwise implied or stated. The internal pin here serves to centre the required filter elements, while the second pin is provided for placing the elastic membrane for the transfer needles. The transfer needles are here received in two bores of the pin protruding to the outside, wherein a transfer needle has a connection to the second pin via a centric through bore, while the second transfer needle permits air supply from outside into the storage bottle via the filter unit. The pot-like intermediate part is closed with a lid.

The lid is here equipped with a third pin which is provided with a Luer-Lock thread, for example to screw on a disposable syringe. The through bore through the pin here ends on one side in the transfer needle and on the other side via the lid in the third pin so that the liquid may be sucked off after the transfer needle has penetrated the seal of the storage container.

The second transfer needle, which also penetrates into the interior of the storage bottle through the seal, here serves to supply air to prevent a vacuum in the storage bottle. The required air is directed from outside into the storage bottle via the filter unit in the pot-like intermediate part.

In a further development, the end part and the lid are connected to each other via locking elements or are optionally welded by laser welding. To form the filter unit, a valve disk, a valve seal, a filter frame with openings, a hydrophobic membrane filter and optionally an activated-carbon filter are arranged in the pot-like indentation of the intermediate part. The valve disk here directly abuts against the valve seal, where the filter frame is inserted afterwards and air may flow into the intermediate part through the openings. The air reaches the interior via the activated-carbon filter and a hydrophobic membrane filter and may thus be discharged into the storage bottle via the transfer needle. By means of the activated-carbon filter, impurities, such as vapours, aerosols, are filtered out of the air, while sterile air may enter the storage bottle through the hydrophobic membrane filter.

In a further development of the invention, the needle protector consists of an elastic material, for example of silicone rubber, which is at one end provided with a bore which directly serves to receive the second pin of the bottom surface. The elasticity of the needle protector ensures that it may be compressed when the transfer device is being placed onto the storage bottle, but will reassume its original shape when the transfer device is removed from the storage bottle, and thereby the transfer needles are completely enclosed. To connect the needle protector and the intermediate part, the needle protector is provided with a bore which may be directly placed onto the second pin of the intermediate part. Here, the needle protector is preferably designed like an accordion to ensure the required elasticity. Preferably, a plastic material is used for the needle protector which is soft and smooth while it simultaneously has a high restoring force. The other end of the needle protector is equipped with a moulded disk which is guided within the housing so as to be axially movable and is adapted to the inner diameter of the cylindrical housing, wherein a cylindrical elevation is formed on the side facing outwards which has a centrical surface. The cylindrical elevation will be penetrated by both transfer needles when the needle protector is being compressed. Moreover, the centrical surface directly abuts against the seal of the storage bottle so that a uniform contact pressure onto the needle protector is created when the transfer device is being shifted onto the storage bottle, and the transfer needles moreover directly come out of the centrical surface and may enter the seal of the storage bottle. To ensure the withdrawal of the fluid/medicine and the air supply, the needle protector is configured to receive two transfer needles, one transfer needle being used for sucking the liquid out of the storage bottle, and the second transfer needle being used for air supply. Insofar, the second transfer needle forms an air duct which leads, via the filter arrangement, to the outside air, and thus the latter enter the storage bottle after having been filtered and cleaned.

In a further particular development of the invention, the air duct is sealed by a valve seal which opens when air is entering and remains in a closed position in case of any overpressure in the storage bottle. The valve seal is to prevent here that, while air bubbles and medicine are pushed back from the disposable syringe, due to an occurring overpressure, droplets of medicine from the storage bottle reach the filter unit via the air duct and affect its function. This in particular prevents that droplets of medicine reach the hydrophobic filter and the latter loses its air permeability at high pressure. By means of the valve seal, however, such wetting of the hydrophobic filter may be prevented, and the functioning of the hydrophobic filter is thereby ensured permanently.

The filter seal with a sealing function in the rest position is achieved by either the valve seal having a one-sided edge swelling, or the filter frame being equipped with an edge-sided bulge. By this measure, the valve seal obtains a pre-tension which results in a sealing of the air duct in the direction from the storage bottle to the air inlet opening. If, in contrast, air is sucked in via the air inlet opening, the valve seal will open and the air may get into the storage bottle via the air duct.

In a further development, the cylinder section comprises, by two diametrically opposed recesses each, a tube wall section formed between the recesses. By the diametrically opposed recesses in the cylinder section, two opposed tube wall sections are formed which are connected with the housing via a web so as to be elastically movable. The tube sections here comprise at one end a locking hook which may directly grip around the neck of the storage bottle, while at the other end, the tube wall sections are equipped with an externally protruding pressing surface so that, while the two pressing surfaces are compressed, the tube wall sections are, at the opposite end, moved radially outwards, whereby the locking hooks may release the neck of the bottle.

The invention will be further illustrated again below with reference to the figures.

DETAILED DESCRIPTION OF THE PREFERRED EMBODIMENTS

Figure 1:
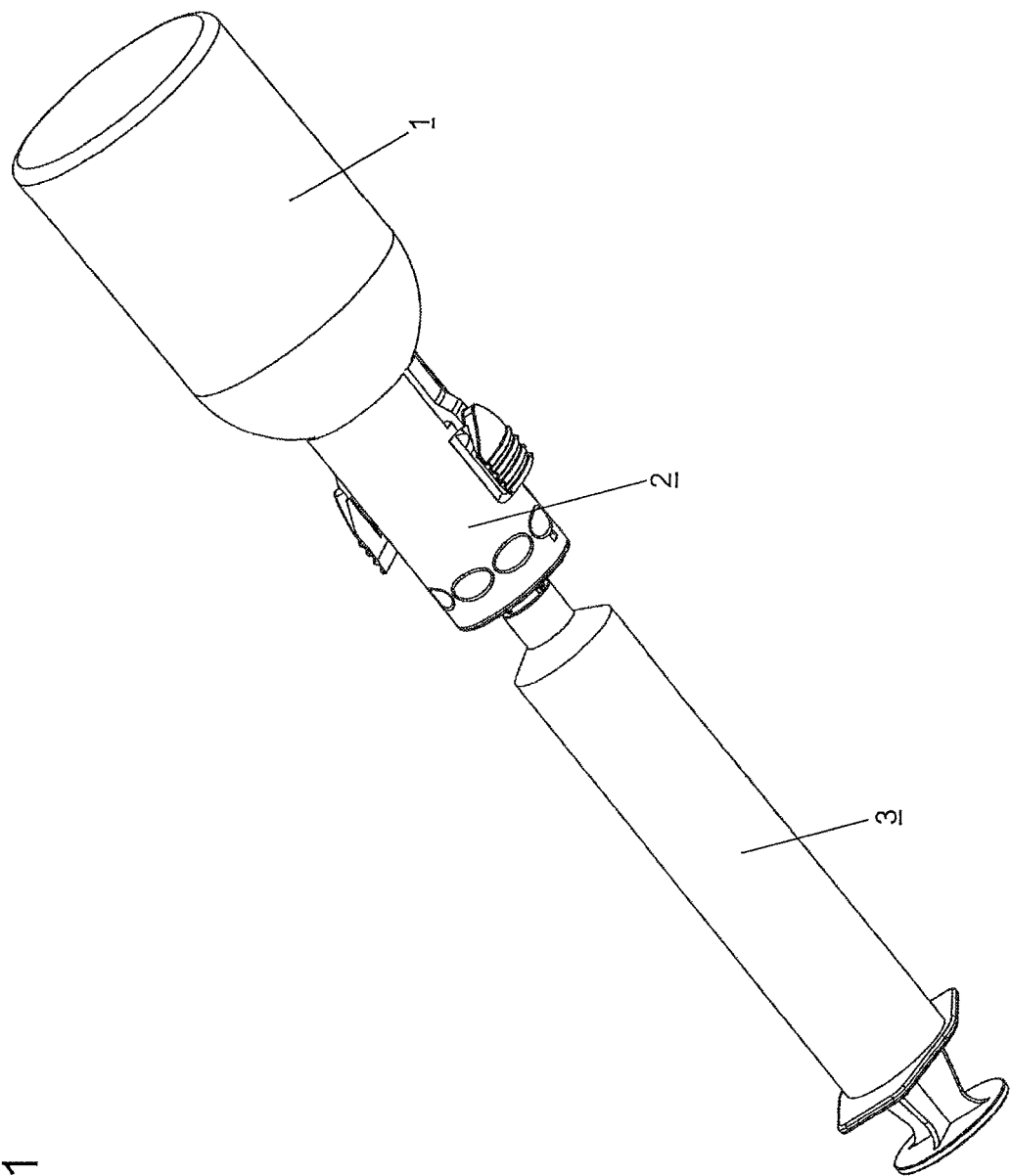
FIG. 1 shows a storage bottle with a transfer device and a disposable syringe placed thereon in a perspective view.

FIG. 1 shows a storage bottle 1 with a transfer device 2 and a disposable syringe 3 placed thereon in a perspective view. The storage bottle 1 consists of a cylindrical glass vessel which is first rounded in the upper region and passes over into a tapering neck of the bottle. The transfer device 2 is placed on this tapering neck of the bottle, wherein furthermore the disposable syringe 3 is screwed on a threaded section of the transfer device 2.

Figure 2:
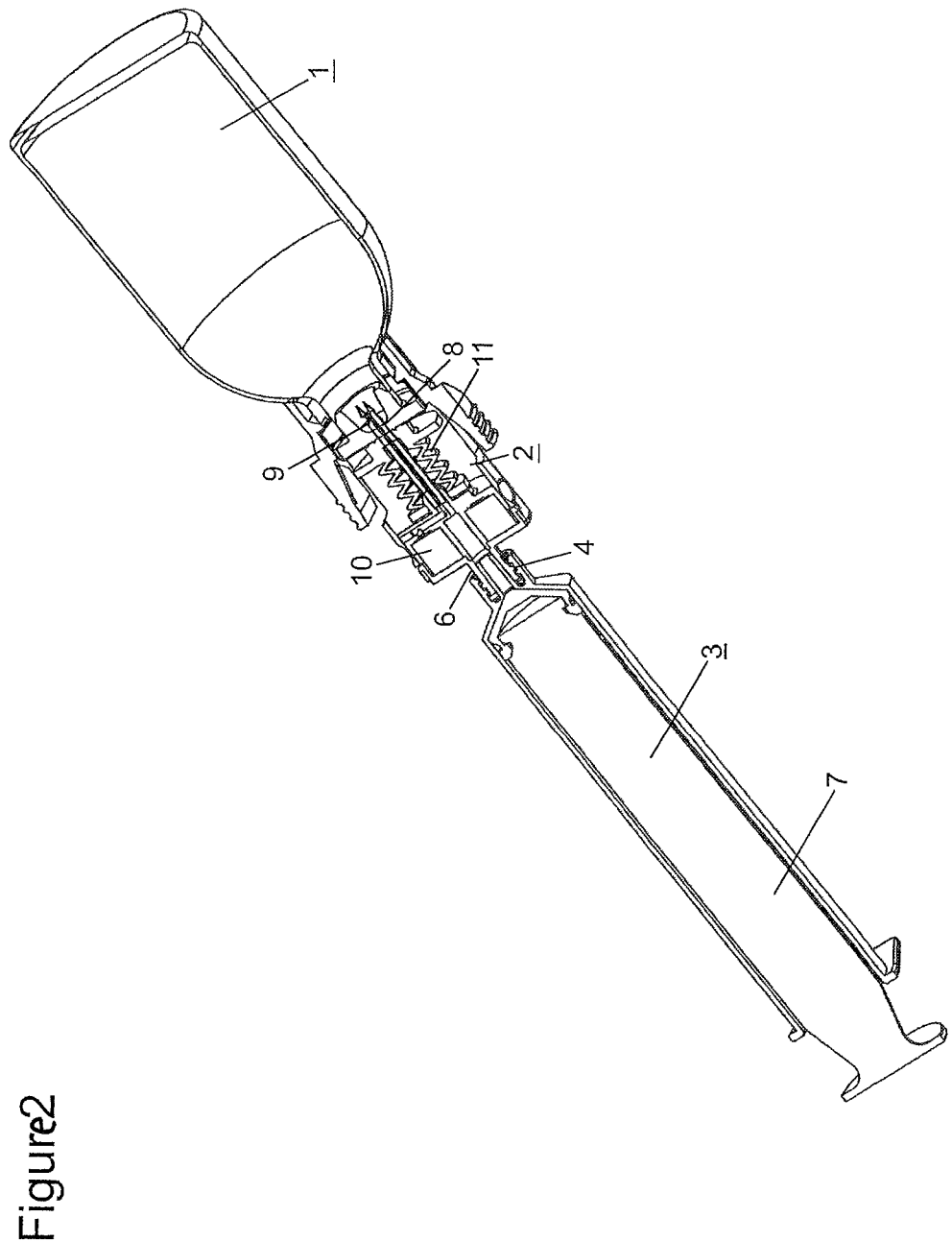
FIG. 2 shows the representation of FIG. 1 in a perspective sectional view.

FIG. 2 shows the arrangement according to FIG. 1 consisting of a storage bottle 1, a transfer device 2, and a disposable syringe 3 in a perspective view. The disposable syringe 3 is here connected to a pin 6 of the transfer device 2 via a Luer-Lock thread 4 so that, when the piston 7 is pulled out, the liquid may be sucked out of the storage bottle 1 via a transfer needle 8. Simultaneously, via a transfer needle 9 and a provided filter unit 10, air from outside may get, via the filter unit 10 and the transfer needle 9, into the interior of the storage bottle 2 to cause pressure compensation. The two transfer needles 8, 9 are here surrounded by a protective covering 11 within the transfer device 2 and come out of a front face of the protective covering 11 when the transfer device 2 is being placed onto the storage bottle 1 due to the fact that the protective covering 11 having an accordion-like shape is simultaneously compressed when it is placed on. If the transfer device 2 is removed from the storage bottle 1 and thus the front face of the protective covering is no longer in contact with the rubber seal of the storage bottle 1, the protective covering will slide back into its original position so that the two transfer needles 8, 9 are completely enclosed by the protective covering 11. Further details of the transfer device 2 are illustrated in the following figures.

Figure 3:
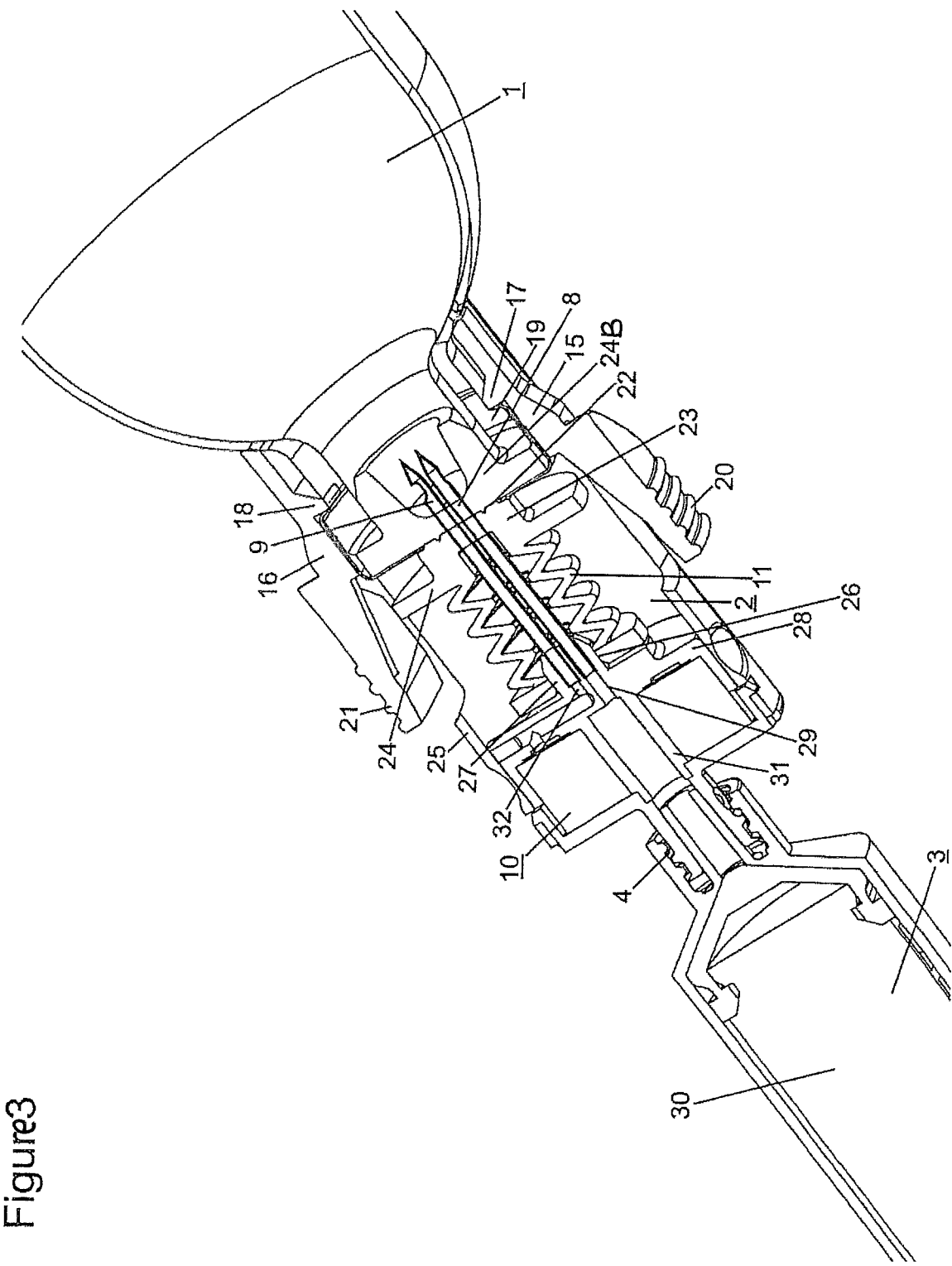
FIG. 3 shows the transfer device in an enlarged representation with the storage bottle and the disposable syringe in a perspective sectional view.

FIG. 3 shows the transfer device 2 with the storage bottle 1 and the disposable syringe 3 in a perspective enlarged view. In this enlarged view, one can see the Luer-Lock thread 4 onto which the disposable syringe 3 has been screwed and which thus forms a liquid-tight connection with the transfer device 2. The storage bottle 1 is supported by two tube wall sections 15, 16 which are provided with a hook 17, 18 at the end. The hooks 17, 18 here grip around the neck 19 of the storage bottle 1. To release the transfer device 2, the tube wall sections 15, 16 each have a pressing surface 20, 21, where during the compression of the pressing surfaces 20, 21, the tube wall sections 15, 16 are moved radially to the outside and thereby the hooks 17, 18 release the neck 19 of the bottle.

When the transfer device 2 is placed onto the storage bottle 1, the front face 22 of the cylindrical elevation 23 abuts against a rubber seal 24B of the storage bottle 1. When the transfer device 2 is pushed further onto the storage bottle 1, the two transfer needles 8, 9 puncture the rubber seal 24 while the protective covering 11 is simultaneously compressed. The protective covering 11 is here guided via a rubber seal 24 within the cylindrical housing 25 of the transfer device 1. The rubber seal 24 and the protective covering 11 are here integrally formed, wherein at least the protective covering 11 is designed to be elastic. The end of the protective covering 11 opposed to the rubber seal 24 has a bore 26 which is placed onto a pin 27 of the intermediate part 28. The pin 27 furthermore serves to receive the two transfer needles 8, 9, the first transfer needle 8 being directly connected with the interior 30 of the disposable syringe 3 via a bore 29. The bore 29 here extends starting from the pin 27 of the transfer needle 8 via a second pin 31 to the Luer-Lock thread 4 and thus into the interior 30.

The second transfer needle 9 serves the air supply for the storage bottle 1 and is also received in the pin 27, wherein a bore 32 leads to a filter unit 10. The filter unit 10 can be seen in FIG. 7 more in detail.

Figure 4:
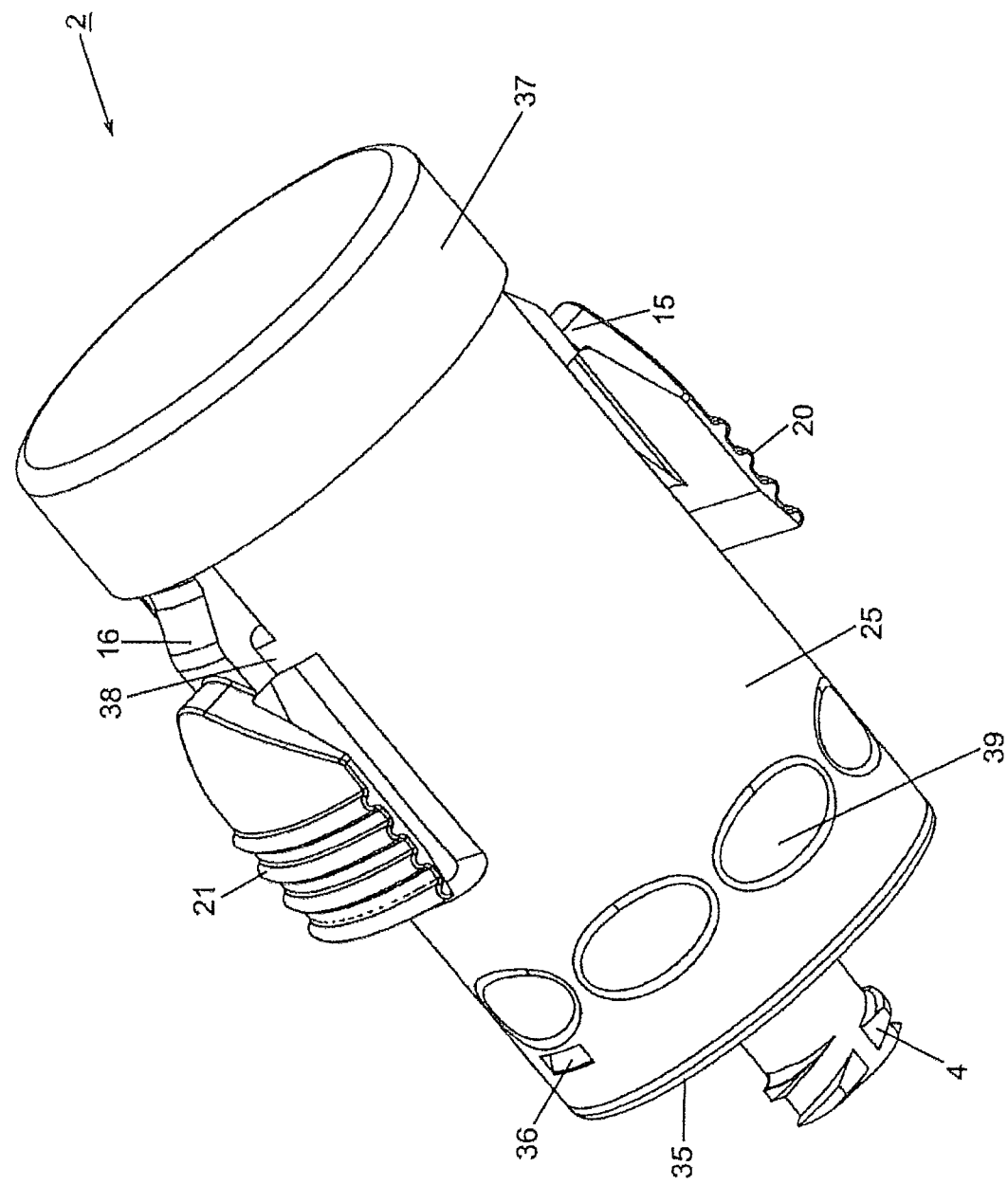
FIG. 4 shows the transfer device in a perspective view.

FIG. 4 shows the transfer device 2, as it is already known from the previous FIGS. 1 to 3, in a side view. The lower end of the transfer device 2 has a Luer-Lock thread 4 onto which the disposable syringe (not shown) may be screwed. The Luer-Lock thread 4 is directly integrally connected with a lid 35 which is connected with the cylindrical housing 25 via two locking hooks 36 distributed across the circumference. As an alternative, it is possible to effect welding, in particular laser welding, between the lid 35 and the housing 25. The opposite end of the housing 25 has the tube wall sections 15, 16 which may grip around the neck of the storage bottle with one hook 17, 18 each not visible in this view. In the representation according to FIG. 4, a protecting cap 37 is placed on the tube wall sections 15, 16 which additionally protects the transfer device 2 from impurities and is removed when the transfer device 2 is employed. To release the transfer device 2 from the storage bottle 1, the tube wall sections 15, 16 are provided with a pressing surface 20, 21 which protrude from the cylindrical housing 25 and are connected with the housing 25 by connection via a web 38 so as to be elastically movable. If trough-shaped indentations 39 are present on the surface of the cylindrical housing 25, these are only used for improving the haptic of the housing 25.

Figure 5:
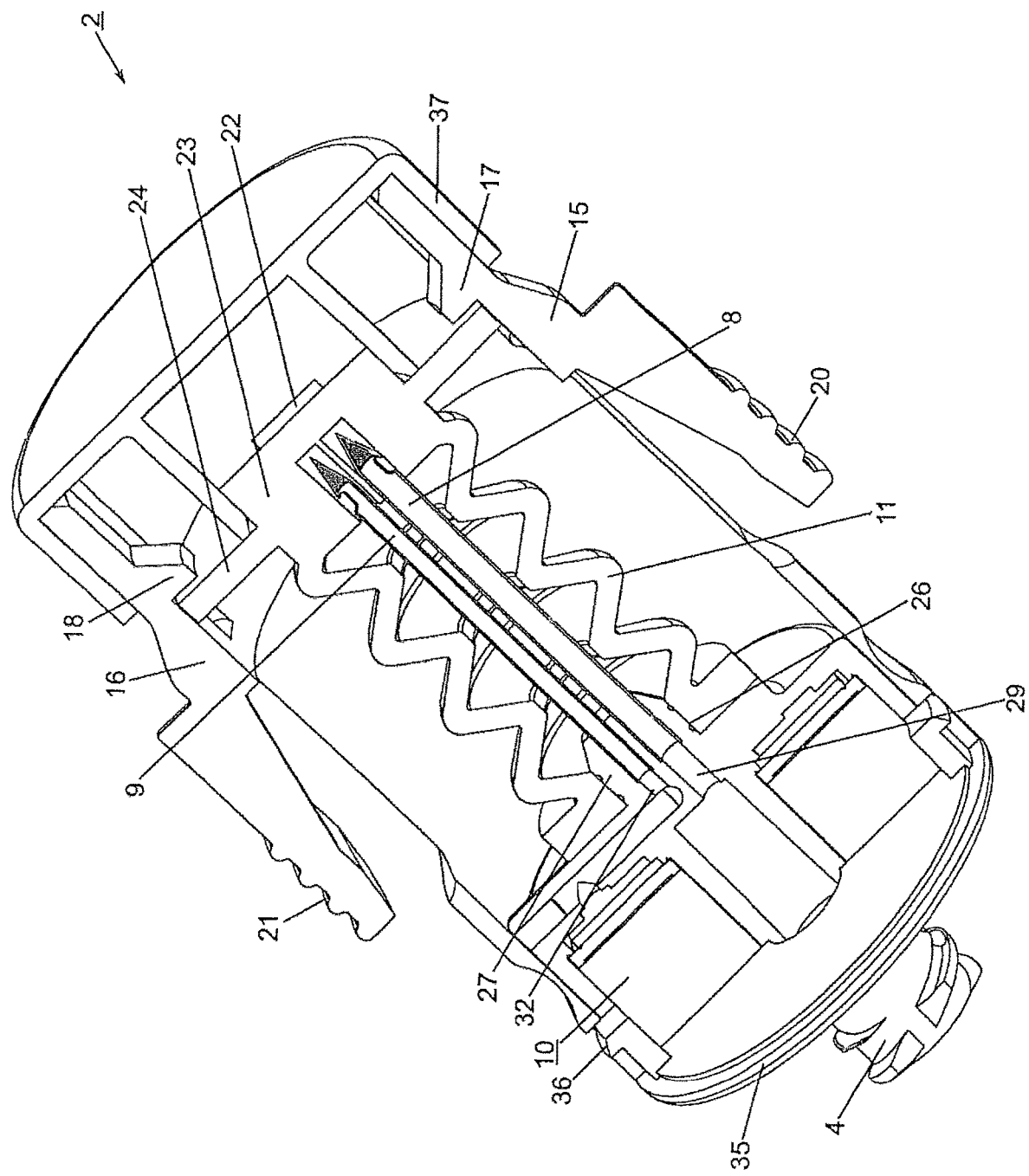
FIG. 5 shows the transfer device in a perspective sectional view.

FIG. 5 shows, in a perspective sectional view, the transfer device 2 according to FIG. 4. The protecting cap 37 is placed on the transfer device 2 and is tightly seated on the cylindrical tube wall sections 15, 16 and may be simply drawn off. For placement onto the storage bottle, the tube wall sections 15, 16 are equipped with the hooks 17, 18 which may grip around the neck of the storage bottle. The movability of the locking elements is here ensured by the pressing surfaces 20, 21 with respect to the cylindrical housing 25 so that, while the two pressing surfaces 20, 21 are compressed, the hooks 17, 18 are moved radially to the outside so that the storage bottle 1 or the neck of the bottle, respectively, are released. The two transfer needles 8, 9 are, when the transfer device 2 is not yet placed on a storage bottle 1, completely surrounded by the protective covering 11, wherein the tips of the transfer needles 8, 9 are received in a recess of the cylindrical rubber seal 24 which simultaneously serves as guidance in the cylindrical housing 25. The cylindrical rubber seal 24 and the protective covering 11 are integrally formed so that, when the protective covering 11 is compressed, the two transfer needles 8, 9 may project from the front face 22, the front face 22 being provided directly for abutment against the seal of the storage bottle 1. The transfer needle 8 is here connected with the bore of the Luer-Lock thread via a bore 29 so that sucked-in liquid will directly get into the disposable syringe. The second transfer needle 9 is in contrast connected with the filter unit 10 via a bore 32 which permits air to enter.

Figure 6:
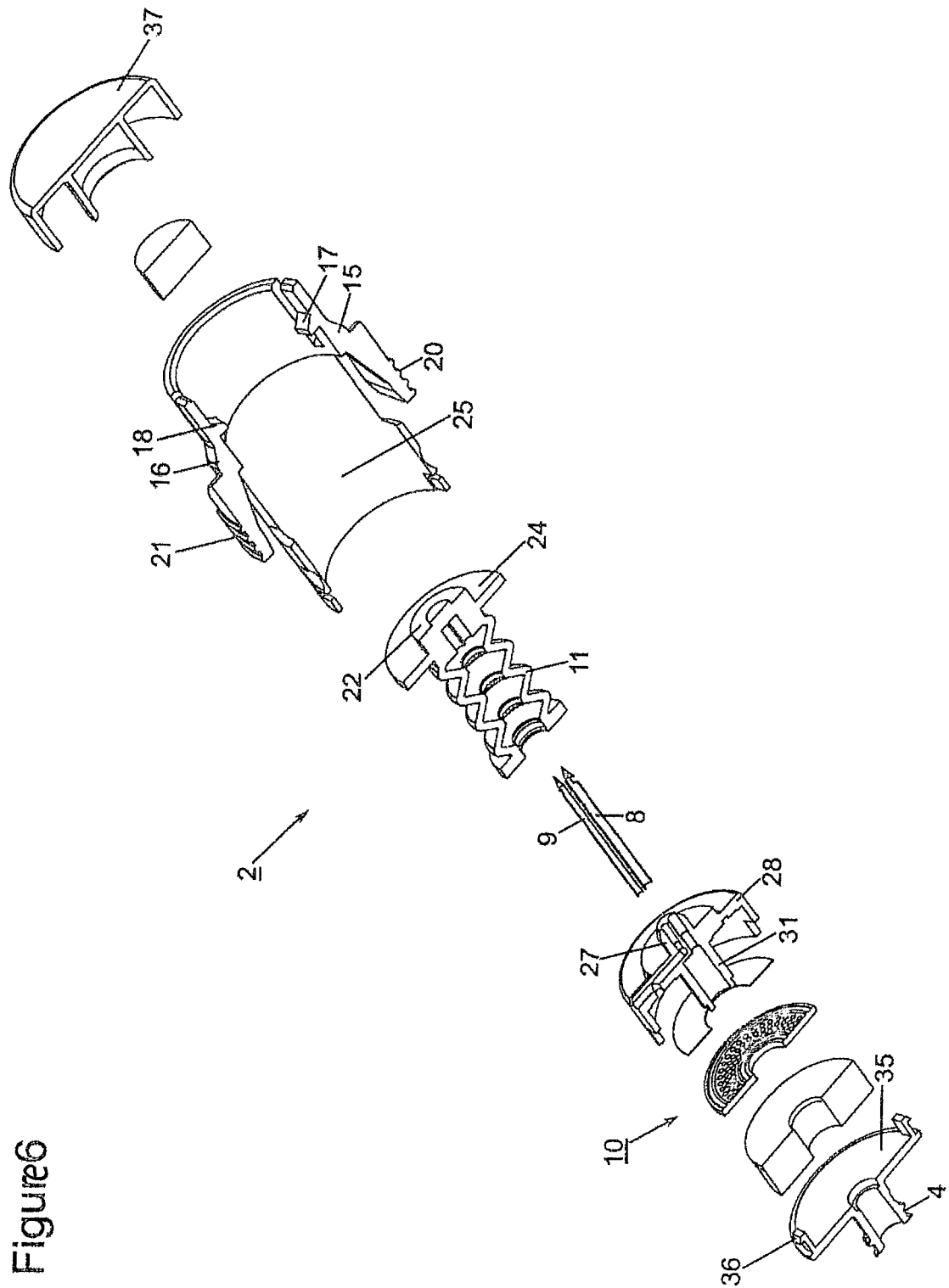
FIG. 6 shows the individual parts of the transfer device in a perspective exploded view.

FIG. 6 shows the individual parts of the transfer device 2 in a perspective exploded view. As was already described in FIGS. 1 to 5, the transfer device 2 consists of a protecting cap 37, a cylindrical housing 25 with tubular wall sections 15, 16 and hooks 17, 18, wherein a release 20, 21 is possible by means of the pressing surfaces 20, 21. Within the cylindrical walls of the housing 25, the protective covering 11 with a rubber sealing 24 is movably held and pulled over the two transfer needles 8, 9 so that any contact is excluded. The two transfer needles 8, 9 can only get out of the protective covering 11 if it is pushed together like an accordion. The pushing together is only effected if the front face 22 abuts against the seal of the storage bottle 1 during placement. An intermediate part 28 serves to receive the filter unit 10, wherein the intermediate part 28 externally comprises a pin 27 which is provided for placing the protective covering 11 and simultaneously receives the two transfer needles 8, 9. A second pin 31 is located within the pot-like intermediate part 28 and permits a centrical accommodation of the individual parts of the filter unit 10. The intermediate part 28 with the filter unit 10 is furthermore closed by a lid 35 which is connected with the intermediate part 28 by means of two locking hooks 36. As an alternative, laser welding is possible. The lid 35 comprises a Luer-Lock thread 4 so that commercially available syringes may be screwed onto this Luer-Lock thread 4.

Figure 7:
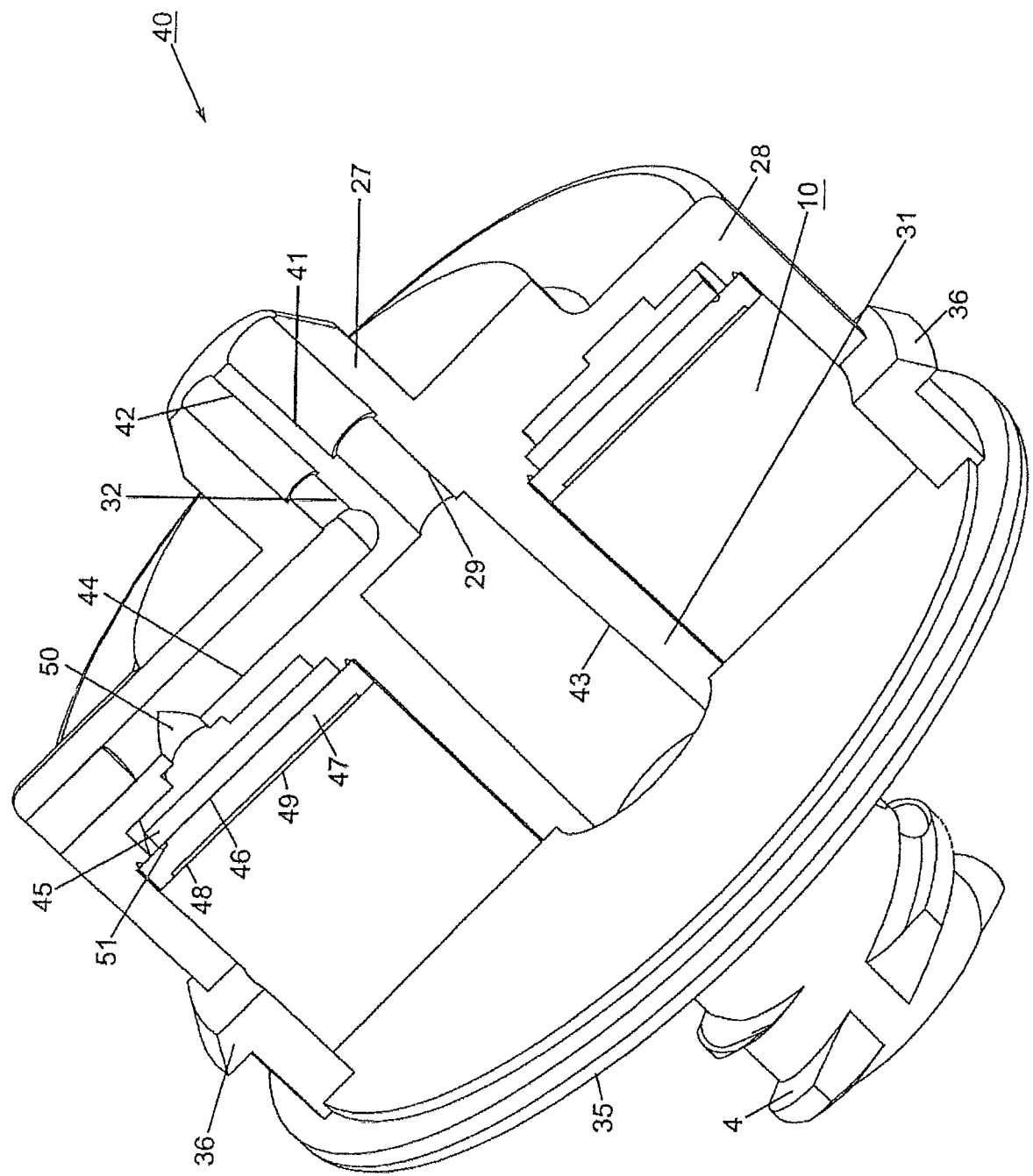
FIG. 7 shows the transfer device in the region of the intermediate part in an enlarged sectional side view.

FIG. 7 shows a housing insert or inset 40 in a perspective sectional view. The housing insert or inset 40 consists of an intermediate part 28 with a filter unit 10 and a bottom 35 to which a Luer-Lock thread 4 is integrally moulded. A pin 27 protruding to the outside is provided for receiving the two transfer needles (not shown), wherein these are received in a bore 41 and 42, respectively. The transfer needles may be, for example, glued into the bore 41, 42. The bore 41 is furthermore followed by a bore 29 having a smaller diameter which directly ends in a fluid channel 43. The fluid channel 43 extends through the external connecting piece of the housing insert or inset 40 so that it ends in a connected disposable syringe with the Luer-Lock thread. Via the bore 29, 41 and the fluid channel 43, there is thus a direct connection from the disposable syringe via the transfer needle to the liquid after the storage bottle has been placed. The second transfer needle is received in the bore 42 which also passes over into a tapering bore 32. The bore 32 initially extends axially, but subsequently passes over into a radial bore 44. The radial bore 44 is guided to the filter unit 10.

The second pin 31, which receives the fluid channel 43, is provided for centring the filter unit 10. The annular space formed by the pin 31 and the outer wall serves to accommodate a valve disk 45 which is supported by a filter frame 47. The filter frame 47 has a recess 48 in which a hydrophobic filter disk 49 comes to lie and includes several openings 52. The valve disk 45 is arranged opposite to an opening 50 of the radial bore 44. To obtain a pre-tension, either the valve disk 45 is provided with a radial bulge 51, or as an alternative, the filter frame 47 may be provided with a comparable bulge. By virtue of the bulge 51, a pre-tension is created onto the valve disk 45 which leads to the air duct being closed in the rest position. This is because the bulge forces the valve disk 45 to flex when in its quiescent state, and the flexure induces within the valve disk a pre-tension, or reactive force, which urges the valve disk against the opposing surface of the filter frame 47 to form a sealing interface along the extent of the bulge where the bulge and the filter frame are in contact.

The flow conditions in normal operation are as follows. Via the Luer-Lock thread 4, the fluid channel 43, the bore 29 and 41 and the transfer needle, there is a direct connection from the disposable syringe to the interior of the storage bottle. Thus, by drawing up the disposable syringe, the medicine may be sucked from the storage bottle. If there are optionally air bubbles in the disposable syringe, these may be put back into the storage bottle by turning the complete transfer device and exerting a pressure onto the piston of the disposable syringe.

To prevent a vacuum from forming in the storage bottle, the storage bottle is connected with the filter unit 10 via the second transfer needle which is seated in the bore 42, via the bore 32, the radial bore 44 and the opening 50. By the valve disk 45 being pre-tensioned, no leakage of liquid from the storage bottle to the filter unit 10 through the provided valve disk 45 is possible. In contrast, for avoiding a vacuum in the storage bottle, air may enter the filter unit 10 via an opening. Through the hydrophobic filter disk 49 and the filter frame 47 with its openings 52 and the valve disk 45, the air gets into the opening 50 and thereby into the storage bottle via the radial bore 44 and the bore 32 and the second transfer needle. This is the normal air supply which, due to the pre-tension of the valve disk 45, only opens when there is a vacuum in the storage bottle. If via the disposable syringe, liquid, and optionally also air bubbles are supplied into the storage bottle and thus an overpressure could be formed in the storage bottle, this overpressure cannot get to the filter unit 10 via the second transfer needle, the bore 32 and the radial bore 44 because the valve disk 45 closes the opening 50. In this manner, it is ensured that no droplets of the medicine can get outside. It is moreover ensured that the hydrophobic filter 49 is not getting clogged by droplets thereby preventing air from entering through the filter unit 10. The admission of air is always required when the liquid is sucked off from the storage bottle.

Figure 8:
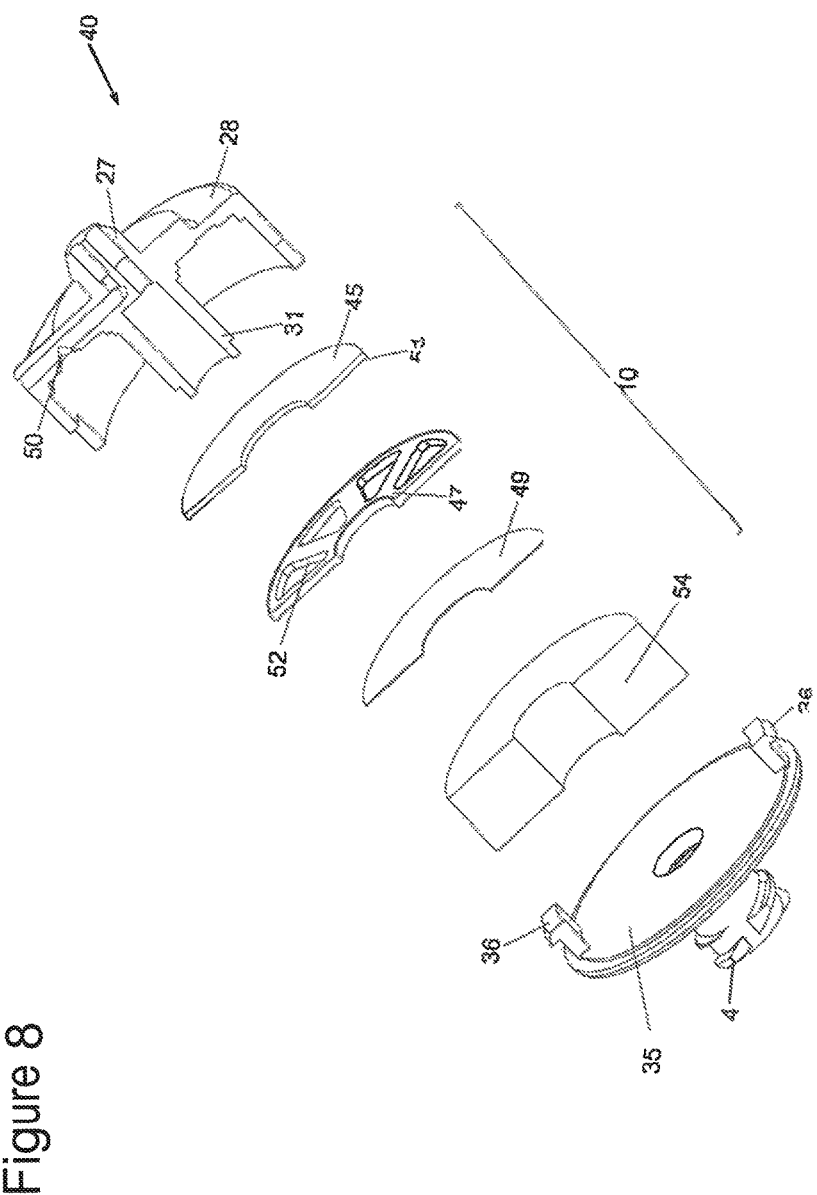
FIG. 8 shows the individual parts of the filter unit in a perspective exploded view.

FIG. 8 shows again the individual parts of the housing insert or inset 40 in a perspective exploded view. The housing insert or inset 40 consists of an intermediate part 28 with a pin 27 protruding to the outside for receiving the two transfer needles and an internal pin 31 which causes the centring of the further materials required for the filter unit 10. The intermediate part 28 has a pot-like design and thus permits to receive the further elements of the filter unit 10, wherein several gradations are present within the intermediate part 28. The opening 50 here first ends in a ring channel 2 where the valve disk 45, for example of silicone rubber, is located which has an annular bulge 51 at the edge. The valve disk 45 is followed by a filter frame 47 which is equipped with openings 52 so that air may flow into the transfer device over a large opening cross-section. Underneath the filter frame 47, a hydrophobic filter disk 49 is received in a recess, followed by a foam filter 54 which is enriched with activated carbon. The intermediate part 28 is closed by a lid 35 which permits a locking with the intermediate part 28 via two locking hooks 36. As an alternative, it is possible, to weld the lid 35 and the intermediate part 28 to each other, in particular by laser welding. The annual cavity of the intermediate part 28 is thus completely filled by the elements of the filter unit 10, and the intermediate part 28 is, after it has been assembled and sealed with the lid 35, slid into the open cylindrical end of the housing 25 of the transfer device 2. In this case, too, the intermediate part 28 may be connected with the housing 25 by means of laser welding so that a solid modular unit is available.

Figure 9:
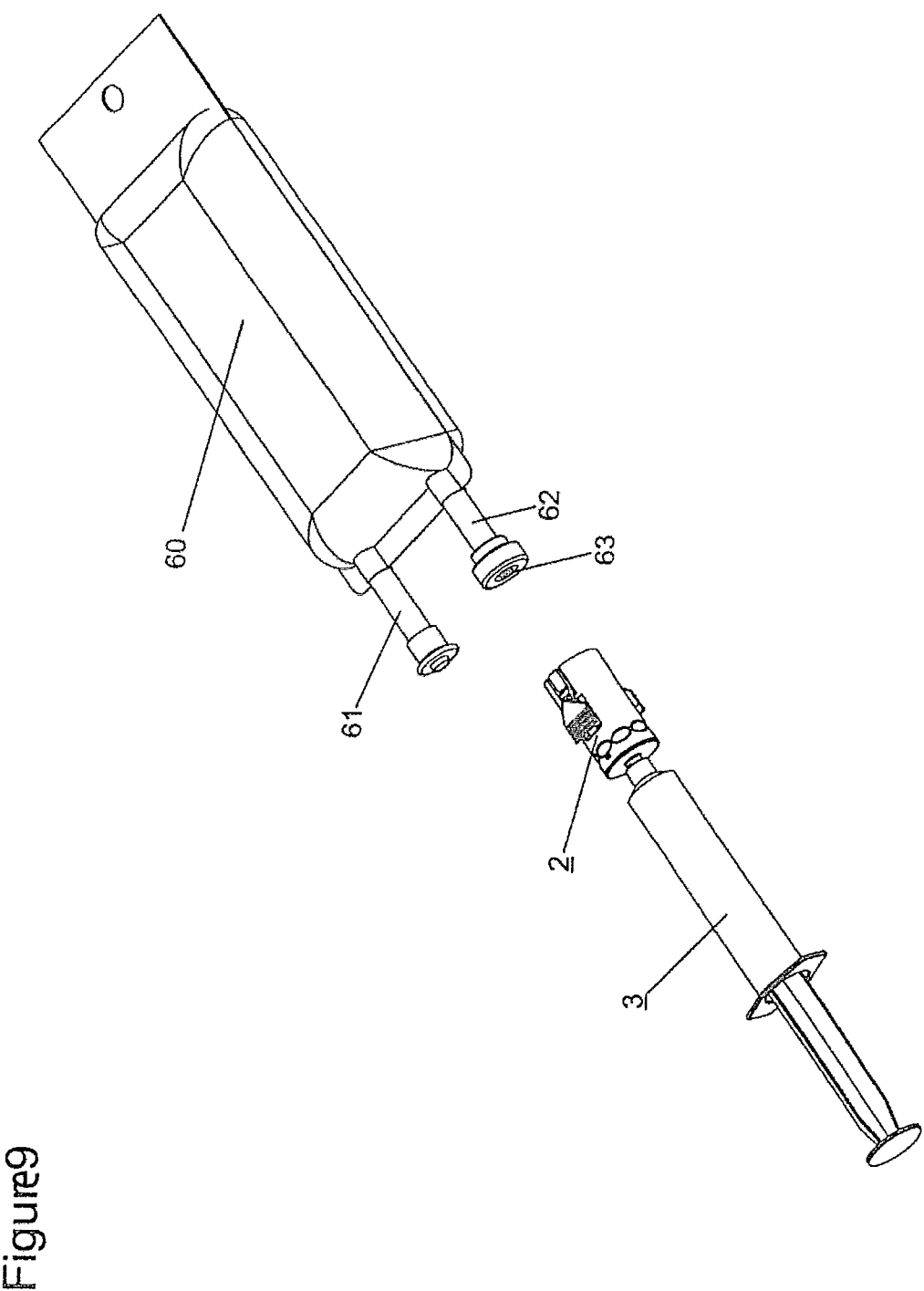
FIG. 9 shows a transfer device with a disposable syringe and an infusion bag before the transfer device is placed in a perspective view.

FIG. 9 shows the transfer device 2 with the disposable syringe 3 known from FIG. 1 in a perspective view after the disposable syringe has been filled. The transfer device 2 here permits the connection to an infusion bag 60. The infusion bag 60 has an outgoing port 61 and an incoming port 62 which is compatible with the transfer device 2. Thus, the prefilled disposable syringe with the transfer device 2 may be placed onto the port 62, and by means of the piston, the medicine may be put into the infusion bag. To this end, the two injection needles are pushed into a seal 63 of the infusion bag by pushing back the protective covering so that they obtain a connection to the interior of the infusion bag 60. Instead of the compatible port, the infusion bag 60 could also be provided with a Luer-Lock thread to be able to directly connect the disposable syringe.

Figure 10:
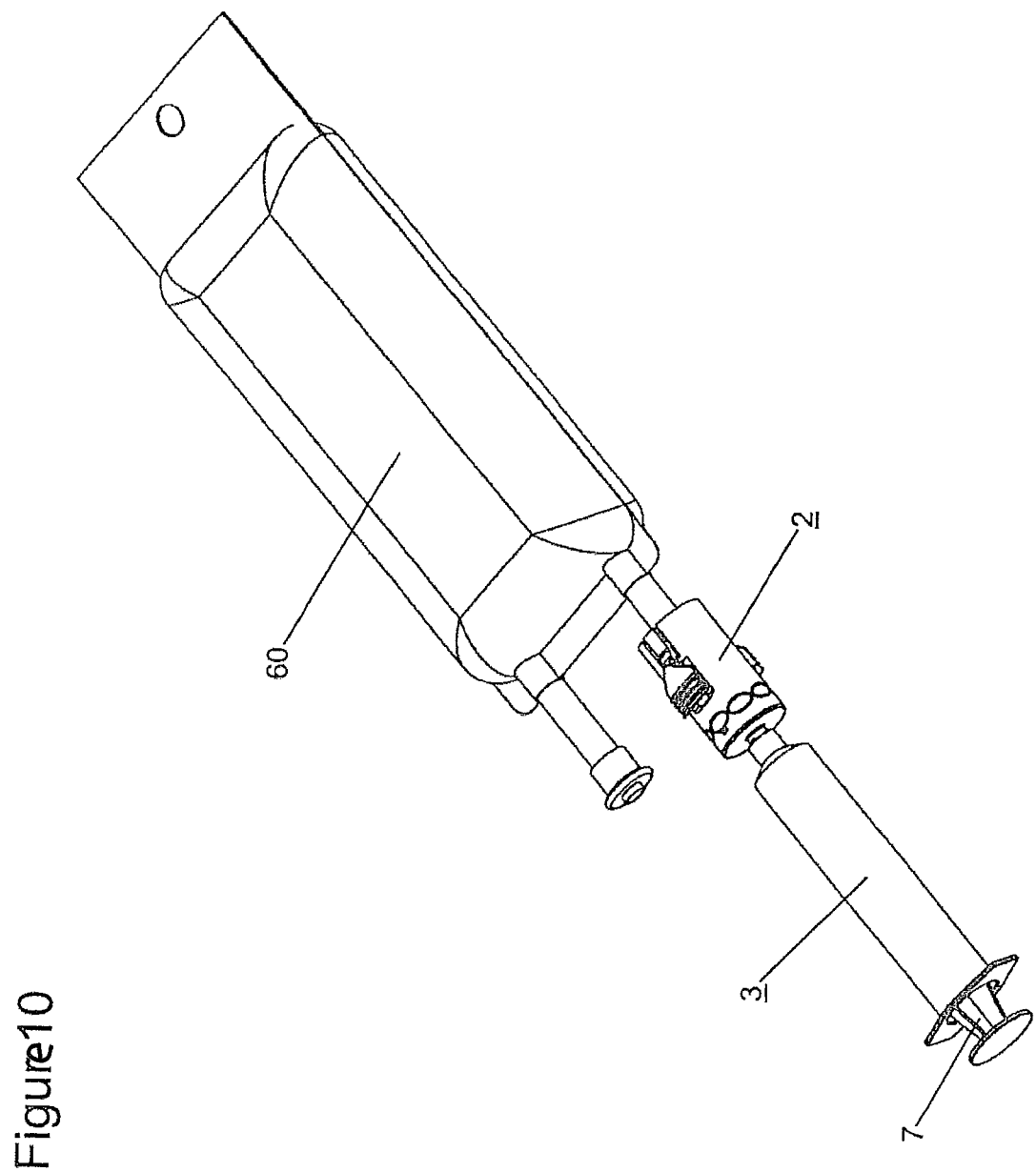
FIG. 10 shows the representation according to FIG. 9 after the transfer device has been placed in a perspective view.

FIG. 10 shows the same arrangement as FIG. 9 in a perspective view after the disposable syringe 3 with the transfer device 2 has been connected to the infusion bag 60, and the medicine has been injected into the infusion bag 60 by means of the piston 7.

LIST OF REFERENCE NUMERALS

1 storage bottle
2 transfer device
3 disposable syringe
4 Luer-Lock thread
6 pin
7 piston
8 transfer needle
9 transfer needle
10 filter unit
11 protective covering
15 tube wall sections
16 tube wall sections 17 hook
18 hook
19 neck of the bottle
20 pressing surface
21 pressing surface
22 front face
23 elevation
24 rubber seal
25 housing
26 bore
27 pin
28 intermediate part
29 bore
30 interior
31 pin
32 bore
35 lid
36 locking hook
37 protecting cap
38 web
39 indentations
40 housing insert or inset
41 bore
42 bore
43 fluid channel
44 radial bore
45 valve disk
47 filter frame
48 recess
49 filter disk
50 opening
51 bulge
52 opening
54 foam filter
60 infusion bag
61 port
62 port
63 seal Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A transfer device (2) for fluid transmission from a storage bottle (1) to a receiving unit, comprising at least one housing (25) with a housing insert (40) comprising two transfer needles (8, 9) and a needle protector, the housing (25) having a tubular design and comprising, at one end, an open cylinder section with at least one locking unit for a storage bottle (1), and at an opposite end an opening (50) for the housing insert (40)
characterized in that
the transfer needles (8, 9) are protected by the needle protector, configured to have an accordion-shape, made of an elastic material, wherein the needle protector is placed on the housing insert at one end and has at the other end an annular rubber seal (24) with an elevation (23) which is provided to place said annular rubber seal against a second rubber seal of the storage bottle (1), creating two seals next to one another, closing off the needle protector, wherein the annular rubber seal has a Shore A hardness no greater than 60% of the Shore A hardness of an accordion-shaped elastic material having a Shore A hardness of 60-80.

2. The transfer device (2) according to claim 1, wherein the housing insert (40) consists of an intermediate part (28), configured in a pot shape, which comprises one integrally moulded first pin and one integrally formed second pin (6, 27, 31) each on both sides of the longitudinal axis of symmetry.

3. The transfer device (2) according to claim 1, wherein a through bore extends through integrally formed pins (6, 27, 31).

4. The transfer device (2) according to claim 1, wherein a first pin (6, 27, 31) is provided for shifting on a needle protector, and/or a second pin (6, 27, 31) is provided within an indentation for centring configured in a pot shape.

5. The transfer device (2) according to claim 1, wherein an indentation configured in a pot shape is closable with a lid (35) to which a third pin (6, 27, 31) with a Luer-Lock thread (4) is integrally moulded.

6. The transfer device (2) according to claim 1, wherein an intermediate part (28) and a lid (35) are connected via locking elements.

7. The transfer device (2) according to claim 1, wherein a valve disk (45), a valve seal, a filter frame (47) with openings (53), a hydrophobic membrane filter and/or an activated-carbon filter are located in an indentation configured in a pot shape.

8. The transfer device (2) according to claim 1, wherein the needle protector consists of an elastic material which comprises at one end a bore (26, 29, 32, 41, 42) which is provided for receiving a second pin (6, 27, 31) of a bottom surface and is configured to have an accordion shape.

9. The transfer device (2) according to claim 1, wherein the needle protector comprises a disc and the elevation (23).

10. The transfer device (2) according to claim 1, wherein the elevation (23) comprises a centrical surface which is punctured by at least one needle, and/or the centrical surface comes to lie against a seal (63) of the storage bottle (1).

11. The transfer device (2) according to claim 1, wherein the needle protector is, when the transfer device (2) is placed onto a storage bottle (1), compressed in the axial direction, and thereby needles come out of a centrical surface.

12. The transfer device (2) according to claim 1, wherein the needle protector is configured to receive two transfer needles (8, 9), one transfer needle (8, 9) being provided for sucking the liquid out of the storage bottle (1), and a second transfer needle (8, 9) being provided for air supply, and/or the second transfer needle (8, 9) forms an air duct which is connected to outside air via a filter arrangement.

13. The transfer device (2) according to claim 1, wherein an air duct is sealed by a valve seal which opens when air enters and remains in a closed position in case of any overpressure in the storage bottle (1).

14. The transfer device (2) according to claim 1, wherein a valve seal is equipped with a one-sided edge swelling, or a filter frame (47) or a filter disk is equipped with an edge-sided bulge (51).

15. The transfer device (2) according to claim 1, wherein the cylinder section comprises, by two diametrically opposed recesses each, a tube wall section formed between the recesses.

16. The transfer device (2) according to claim 1, wherein a tube wall section is equipped at one end with a locking hook (36) and comprises at the other end a pressing surface (20, 21) protruding from the tube wall section, and/or the tube wall section is only connected with the housing (25) via a web (38) in an elastically movable manner.

* * * * *